United States Patent
Jones et al.

(10) Patent No.: US 6,516,324 B1
(45) Date of Patent: Feb. 4, 2003

(54) WEB-BASED REPORT FUNCTIONALITY AND LAYOUT FOR DIAGNOSTIC IMAGING DECISION SUPPORT

(75) Inventors: Jeffrey R. Jones, Gold Hill, OR (US); Arvind Taranath, Milpitas, CA (US); Michael P. Ryan, Wauwatosa, WI (US)

(73) Assignee: GE Medical Technology Services, Inc., Waukesha, WI (US)

( * ) Notice: Subject to any disclaimer, the term of this patent is extended or adjusted under 35 U.S.C. 154(b) by 177 days.

(21) Appl. No.: 09/585,226

(22) Filed: Jun. 1, 2000

(51) Int. Cl.[7] ............................................. G06F 17/30
(52) U.S. Cl. ....................... 707/104.1; 707/10; 707/102
(58) Field of Search ................................ 707/104.1, 10, 707/102; 700/764, 773, 804, 843; 378/114; 128/923

(56) References Cited

U.S. PATENT DOCUMENTS 5,864,871 A * 1/1999 Kitain et al. .................. 707/10
6,004,276 A * 12/1999 Wright et al. ................ 128/923
6,325,540 B1 * 12/2001 Lounsberry et al. ........ 378/114

* cited by examiner

*Primary Examiner*—Diane D. Mizrahi
(74) *Attorney, Agent, or Firm*—Ostrager Chong & Flaherty LLP

(57) ABSTRACT

A method and a system for providing remote access to scanner utilization or diagnostic imaging reports generated by a computer system having access to a database of collected scanner operational data. Preferably, the reports are delivered over a wide-area network, e.g. the Internet, in response to requests for access from customers. In particular, the system includes a graphical user interface which allows the user to specify all of the report content parameters and display the report on a single screen. The report content parameters section of the screen allows the user to identify the facility, organization area (i.e., department), equipment, time dimension, time frame, metrics and data slices that the user wants included in the report. The report produced will contain the information currently in the database, which information is updated daily.

24 Claims, 3 Drawing Sheets

WEB-BASED REPORT FUNCTIONALITY AND LAYOUT FOR DIAGNOSTIC IMAGING DECISION SUPPORT

FIELD OF THE INVENTION

This invention relates generally to centralized generation of reports which compile and/or summarize operational data from remotely located user-operated electronic devices, for example, imaging devices used for medical diagnosis.

BACKGROUND OF THE INVENTION

Diagnostic imaging systems are ubiquitous in modern health care facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities.

Currently, a number of modalities exist for medical diagnostic imaging systems. These include computed tomography (CT) systems, x-ray systems (including both conventional and digital or digitized imaging systems), magnetic resonance (MR) systems, positron emission tomography (PET) systems, ultrasound systems, nuclear medicine systems, etc. In many instances, these modalities complement one another and offer the physician a range of techniques for imaging particular types of tissue, organs, physiological systems, etc. Health care institutions often arrange several such imaging systems at a single facility or at multiple facilities, permitting its physicians to draw on such resources as required by particular patient needs.

Modern medical diagnostic imaging systems typically include circuitry for acquiring image data and for transforming the data into a useable form, which is then processed to create a reconstructed image of features of interest within the patient. The image data acquisition and processing circuitry is referred to as a "scanner" regardless of the modality if physical or electronic scanning occurs as part of the imaging process. The particular components of the system and related circuitry, of course, differ greatly between modalities due to their different physics and data processing requirements. The terms "scanner", "medical imaging device" and "diagnostic imaging device" will be used interchangeably herein.

Medical diagnostic systems of the type described above are often called upon to produce reliable and understandable images within demanding schedules and over a considerable useful life. To ensure proper operation, the systems are serviced regularly by highly trained personnel who address imaging problems, configure and calibrate the systems, and perform periodic system checks and software updates. Moreover, service offerings have been supplemented in recent years by service centers capable of contacting scanners at subscribing institutions directly without the need for intervention on the part of the institution personnel. Such centralized servicing is intended to maintain the diagnostic systems in good operational order without necessitating the attention of physicians or radiologists, and is often quite transparent to the institution.

In certain centralized servicing systems, a computerized service center will contact a scanner via a network to check system configurations and operational states, to collect data for report generation, and to perform other useful service functions. Such contacts can be made periodically, such as during system "sweeps", in which a variety of system performance data is collected and stored with historical data for the particular scanner. The data can then be used to evaluate system performance, propose or schedule visits by service personnel, and the like.

While such service techniques have proven extremely valuable in maintaining diagnostic systems, further improvements are still needed. Although the transparency of interactions between scanners and service centers avoids distracting medical personnel with service updates unnecessarily, some degree of interaction between service centers and institutions is highly desirable. In particular, an interactive service system facilitates valuable exchanges of information, including reports of system performance, feedback on particular incidents requiring attention, updates of system licenses, software, imaging protocols, etc. Currently available service systems permit such interactive exchanges. In particular, a platform has been developed that serves as a base for the interactive servicing needs of different modalities. This platform allows a central service center to exchange information on possible service problems with remotely located scanners, and to retrieve information or data log files from scanners for the purpose of servicing those scanners. One known platform provides a uniform interface permitting clinicians and radiologists to operate a variety of scanners in different modalities, and to report service issues for the scanners, via a uniform, intuitive format.

The known integrated user-interactive platform for servicing diagnostic equipment at remote locations may be configured in software, hardware, or firmware at the scanner or may be installed in a central operator's station linking several scanners in a medical facility. The user interface permits service requests to be generated prior to, during or subsequent to examinations executed on the diagnostic equipment. The user interface also permits service messaging, report generation and retrieval, etc. The user interface is preferably configured as a network browser, which also facilitates linking the scanner or the central facility control station to a network such as an intranet or internet. The same user interface may be integrated into scanners of different modalities, thereby further facilitating service requests and the like by operations personnel, without requiring the personnel to become reacquainted with diverse interfaces in a facility.

In particular, the existing user-interactive platform provides the system user with the capability to request scanner utilization reports from a central service center based on the operational history of scanners at a remote facility. In order to provide such utilization reports, it is necessary to regularly collect operational data from these scanners, e.g., via telephone lines or networks.

In accordance with an existing system, every time a customer enters into a service contract to receive scanner utilization reports based on logged data from scanners, customer information and contract specifications are entered into a service contract database, as with any other service feature provided by the central service facility. Each scanner under contract can be programmed to collect its own operational data in computer memory and then proactively transmit that data to a central facility in accordance with a preprogrammed schedule input to the scanner by the central facility. Only scanners covered by a service contract which provides for data logging and report generation will transmit logged operational data to the central facility. After the central facility has collected and processed the log files of operational data from the scanners, scanner utilization reports can be generated. In particular, a hospital administrator can at any time request, via a wide-area network or the Internet, a utilization report compiling and/or summarizing collected operational data for scanners at that hospital. A report server for providing web-based utilization reports may be located far away from the central service facility where data log files are received.

The methods by which users define the content of complex reports are often involved and confusing, especially to novice users. Another problem is that reports generated from data warehouses are often created in advance and stored, which means that the data included in the reports may not be the most recent. In addition, dynamic database reports often take a long time to be displayed, leading to user dissatisfaction. In order to provide web-based scanner utilization reports that meet all of the reporting needs of even inexperienced users, a system must be developed that provides data access flexibility, an intuitive user interface and exceptional report data retrieval and display performance.

SUMMARY OF THE INVENTION

The invention is directed to a method and a system for providing remote access to scanner utilization or diagnostic imaging reports generated by a computer system having access to a database of collected scanner operational data. Preferably, the reports are delivered over a wide-area network, e.g. the Internet, in response to requests for access from customers. In particular, a preferred embodiment of the system comprises a graphical user interface which allows the user to specify all of the report content parameters and display the report on a single screen. The report content parameters section of the screen allows the user to identify the facility, organization area (i.e., department), equipment, time dimension, time frame, metrics and data slices that the user wants included in the report. The report produced will contain the information currently in the database, which information is updated daily. To meet usability needs, the report is easy to understand and is presented virtually immediately (e.g., in less than 5 seconds).

The preferred embodiment of the invention combines a user interface design with a set of data access mechanisms that result in an intuitive user interface and reporting features that are flexible and fast. The report screen contains an area, covering a majority of the screen and extending from one side of the screen, in which the report chart or graph is displayed. The remaining portion of the screen on the other side contains all of the definable report content parameters which can be specified by the user. The user specifies the desired report content parameters and then clicks a virtual activation button to display the report in the report area of the screen. Each of the report content parameter options displays a dynamic list containing the most recent data in the database. In particular, a scanner drop-down pick list will identify every activated scanner in a particular set defined by other parameters.

In accordance with a further aspect of the preferred embodiment, when the user logs in, the report content parameters default to the settings the user chose during that last session when the user requested a report. The time period parameter defaults to the most recent date for which data is present for the selected parameters. A user can specify whether he/she wants to see a trend report, showing data values over time, or a comparison report, showing the values for all the different attributes for a metric for a particular time period. The preferred reporting database uses OLAP (On-Line Application Processing) technology to meet the data flexibility and performance requirements. The data is presented as a chart.

In accordance with the preferred embodiment of the invention, all report content definition options and the report generated from those defined report content parameters are shown on a single web page. The report content definition is established in a top-down hierarchical fashion. The user can quickly and easily specify the content, metrics and data slices that the user wants to see on the screen. The report data retrieval and display process is extremely fast, resulting in increased end user productivity and satisfaction.

DETAILED DESCRIPTION OF THE PREFERRED EMBODIMENTS

The present invention is directed in part to a system and a method for providing information to support the work, process, patient flow and clinical practice of a radiology department. Each scanner in the radiology department sends operational data to a central server for processing. The data collected will measure the key scanner parameters based on key department productivity, quality and patient satisfaction goals and objectives. Based on the data collected, scanner utilization reports are generated at a central location. These reports can be accessed by customers via the Internet or another widearea network. The devices most pertinent to the present invention include computerized tomography (CT) systems, magnetic resonance (MR) systems, ultrasound imaging systems, or any other type of computerized medical imaging device. However, generally the invention has application in user-operated electronic equipment having the ability to log data indicating how the equipment is being used.

Figure 1:
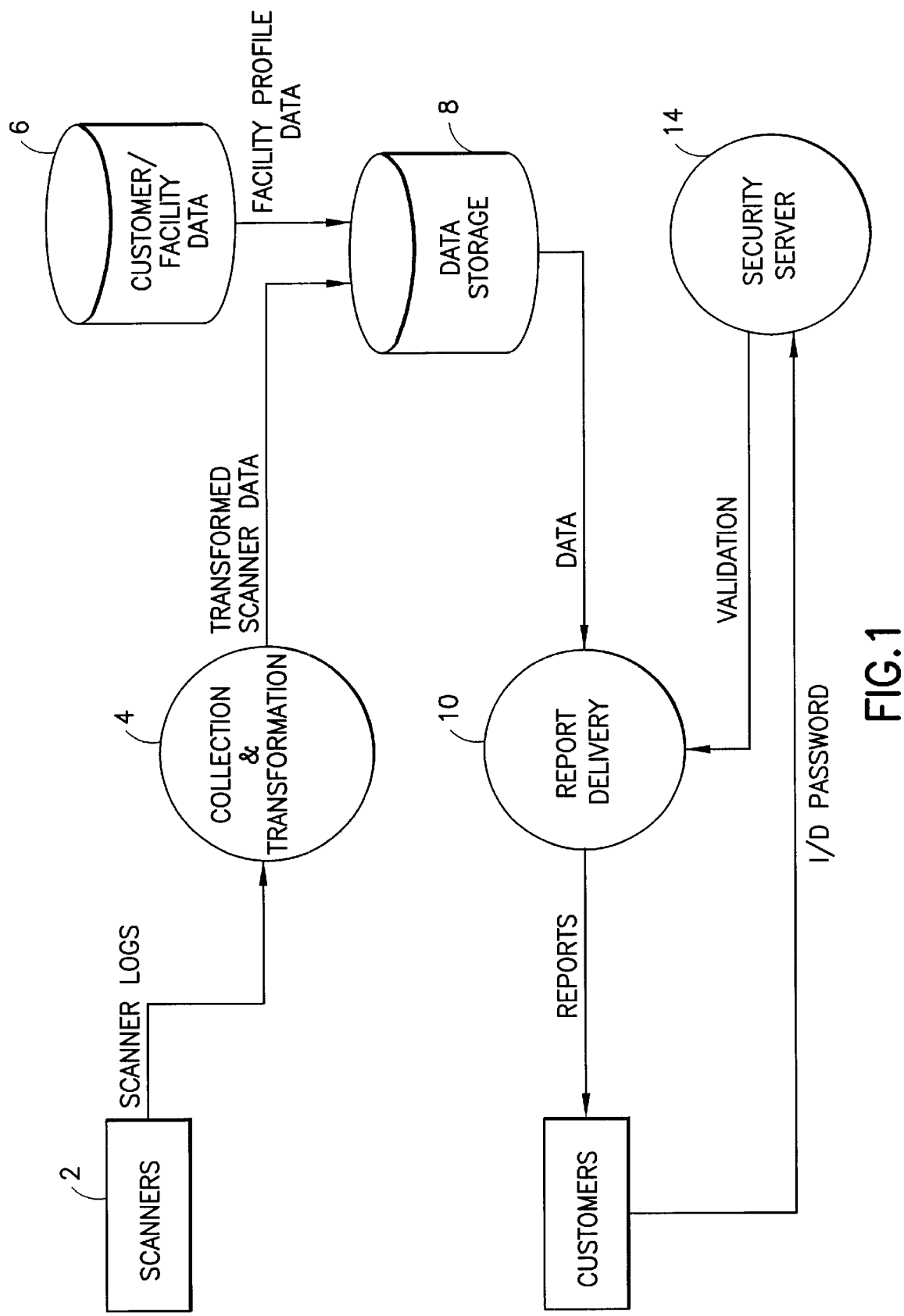
FIG. 1 is a diagram showing the flow and processing of operational data from remotely located scanners in accordance with the preferred embodiment of the present invention.

The high-level flow of data and processing is shown in FIG. 1. Each scanner 2 sends logs of operational data to a central processor 4 for collection and transformation. The transformed data is stored in data storage 8, along with medical facility profile data read from a customer/facility database 6. The stored data is periodically sent to a report delivery system 10. Customers 12 can access those reports provided they have inputted valid and authentic security factors (e.g., ID and password) to a security server 14. The security server sends the validation to the report delivery system 10.

Figure 2:
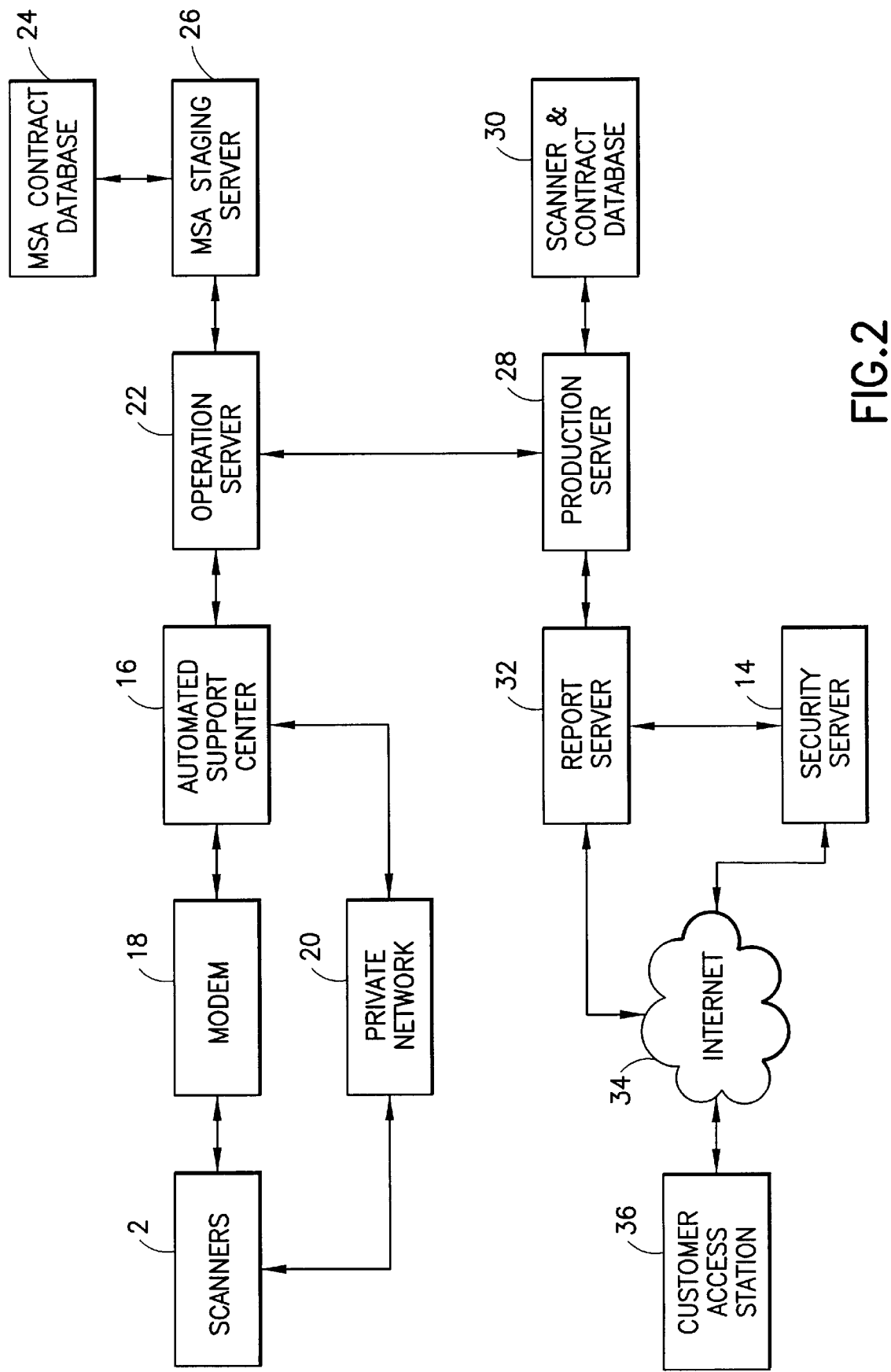
FIG. 2 is a block diagram showing the architectural component interaction of the system in accordance with the preferred embodiment of the invention.

Referring to FIG. 2, data is collected from each scanner 2 by an automated support center server 16 via a modem 18, a private network 20, or any other suitable communications channel. Each scanner is programmed to log specified operation-related data and then send that logged data to the automated support center server 16.

The preferred scanner output format comprises system data and exam data. The system data includes, but is not limited to, a time stamp indicating when a new exam began, the scanner modality, the product name, a system ID (i.e., a unique ID for a scanner for a particular customer at a particular location), a so-called Unique System Number (a unique key for a scanner, regardless of time, location and ownership), a so-called Mobile Location Number (used to track the particular location of the scanner at a particular time), and the hospital name. The exam data includes, but is not limited to, the same time stamp, the exam date, the start and end times for the exam, an exam number, a patient ID, patient age, patient sex, patient weight, patient history, patient status, a radiologist ID, a referring ID, an operator ID, an exam description, and exam data. The scanner transfers this data to the automated support center server 16 using a proactive diagnostics transfer mechanism. The scanner will use a data logging service ID when doing the proactive diagnostic data transfer mechanism. The scanner is programmed to transfer this data based on the time since the last transfer or when the data reaches a specified size threshold. The maximum time between transfers and the data size threshold are configurable per scanner. Also the time when the operational data is sent to the automated support center server is configurable per scanner.

The automated support center server 16 stores the scanner data files by USN, MLN or a combination of the two. The automated support center server 16 notifies an operation server 22 whenever a new file arrives, that was sent with the data logging service ID, by sending the file to the operation server via an internal network of the service provider. The automated support center server 16 logs an error message and notifies the appropriate system administrator if it cannot successfully send the data file to the operation server 22. The automated support center server 16 also provides a mechanism that allows the system administrator to remotely enable or disable the data logging feature and proactive diagnostics data transfer on a scanner system that is authorized to have its logged data reported pursuant to a valid service contract. When a scanner site is activated or deactivated, the automated support center server 16 notifies the operation server 22 with the new state of scanner site.

Every time a customer enters into a service contract to receive scanner utilization reports based on logged data from scanners covered by the contract, the customer profiling information and contract specifications are entered into a service contract database, as with any other service feature provided by the central service facility. This customer profiling and service contract information can be automatically and periodically extracted from a central service contract database and compared by the operation server 22 to a table of customer profiling and contract information in a local database maintained by the operation server 22. Any differences between the records of the respective files are entered in the local database, i.e., new and changed records are added to the local database, while records corresponding to expired service contracts are removed from the local database. New scanners that were not previously recorded in the local database are tracked for contract start date. Existing scanners that are recorded in the local database, but which are covered by an expired service contract, are tagged for turn-off of their data logging functionality.

Once data logging begins, the operation server 22 validates the scanner files upon mail notification from the automated support center server 16 that a scanner data logging file has arrived. The validation comprises the following steps: identifying the file "grammar" (e.g., MR or CT); and verifying that all fields for the service product are present in the record and are of the correct type. If the record is not complete (i.e., missing field) or incorrect, it will be logged and deleted. The operation server 22 generates a CPT code based on scanner file data field values. The operation server 22 also encodes the required fields in a specified XML format. The operation server 22 sends processed (i.e., transformed) scanner files in a compressed XML format to the production server 28 via the internal network of the service provider as soon as the files are processed.

The operation server 22 also records which scanner sites are sending data, the amount of data sent and the time the data was received. The operation server maintains an active site list/database, which is driven by contract information relating to maintenance service agreements (MSA). The MSA service contract information is received daily by the operation server from the MSA staging server 26 via the internal network of the service provider The server 26 in turn retrieves the contract information from an MSA contract information database 24. The operation server 22 notifies the system administrator if a scanner site in the active list has not sent a file in more than a configurable time period. Also, the operation server 22 serves a web page, intended for use in system administration, that displays a history of data reception frequency and data file size on a per scanner basis.

Still referring to FIG. 2, the data storage 30 receives XML-encoded scanner data from the production server 28 whenever the data is sent by the operation server 22. Derived data values such as the inter-exam time and exam duration are computed by the production server 28 and stored in the database 30. The data storage 30 also receives XML-encoded updated facility profile data from the production server 28 whenever that data is sent by the operation server 22.

In accordance with the preferred embodiment of the invention, the security server 14 is physically separate from the report server 32. The security server database is separate from the report server application database. Customer access (36) to all reports is through a so-called Secure Socket Layer (SSL) on the Internet 34. The customer must upload a user ID and password or access code, via the Internet 34, to the security server 14. All user passwords and/or access codes are encrypted. The security server 14 validates users, determines their community membership, and assigns access privileges. Access privileges may be which reports are available to a customer based on that customer's service contract. The security server 14 allows validated users access to appropriate reports served from the report server 32 and transmitted to the customer's access station via the Internet 34.

All utilization reports generated by the report server 32 are based on the scanner data delivered to the production server 28. All graphical reports support a configurable display option that changes the appearance of the output (pie chart, bar chart, etc.). Preferably, the report server 32 delivers utilization reports which are compatible with Internet Explorer 4.01 or greater and Netscape 4.5 or greater on a Windows 95/98/NT platform. If the client is not compatible, then a message is sent to the user and a link to a compatible browser is displayed. The report server is also programmed to provide a configurable selection of time axes for reports. The report server generates reports that show trending and reports that show comparative values.

Multiple report templates are supported. These may be grouped, each group including a number of reports. Access to groups may be based on user access. For example, the report server can generate and deliver reports that show Avg Image Count by Radiologist, Avg Image Count by Study Type, Avg Series Count by Study Type, Avg Study Duration by Study Type, Avg Study Image Count by Technologist, Contrast Used % by Study Type, Study Volume by Hours, Study Volume by Operator, Study Volume by Physician, Study Volume by Radiologist, Study Volume by Study Type, Exam Volume by Patient Age, Exam Volume by Patient Gender, Exam Volume by Patient Mix, Avg Exam Duration by Patient Mix, Avg Exam Duration by Radiologist, Avg Exam Duration by Technologist, Avg Study Duration by Radiologist, Avg Study Duration by Technologist, Avg Time Between Exams, Avg Time Between Exams by Study, Exam Volume by Ordering Physician, Exam Volume by Radiologist, Exam Volume by Technologist, Total Exam Volume, Total Series Volume, Avg Total Duration per Day, and Avg Scanner Utilization.

The preferred embodiment of the invention is a web-delivered service product/capability that gives radiology departments critical decision support information for clinical practice (study, mix), operations management (volume, utilization), and customer demographics analysis (referring physician, patient age, etc.) centered on the "exam" step of patient service delivery.

In accordance with the preferred embodiment of the invention, a user may define parameters of a desired scanner utilization report by navigating to a service center home web page (not shown) and then clicking on a Standard Reports link on the home web. This causes the Standard Reports web page 40, shown in FIG. 3, to be displayed on the user's workstation display screen. Web page 40 includes a rectangular area 42 on the left side for displaying a chart. The right side of web page 40 displays a plurality of user-interactive fields which the user can click on to cause a respective drop-down pick list to appear. In the example shown in FIG. 3, fields 44, 46, 48, 50, 52, 56, 58, 60, 62, and 64 are activatable to reveal a respective hidden drop-down pick list for choosing a respective report content definition option, such as facility, department, modality, scanner, report category, report name, chart type, data slice, and relevant time period covered by the report. The starting date for the period covered by the report appears in field 54. After the report parameters have been defined, the user can click on the Display Chart activation field 66 to cause the system to generate a chart and a tabular report in accordance with the defined parameters, and to display the chart in display area 42. The user can navigate to another web page which displays the generated tabular report by clicking on the Display Data Details link in the lower left-hand corner of the display screen shown in FIG. 3.

Figure 3:
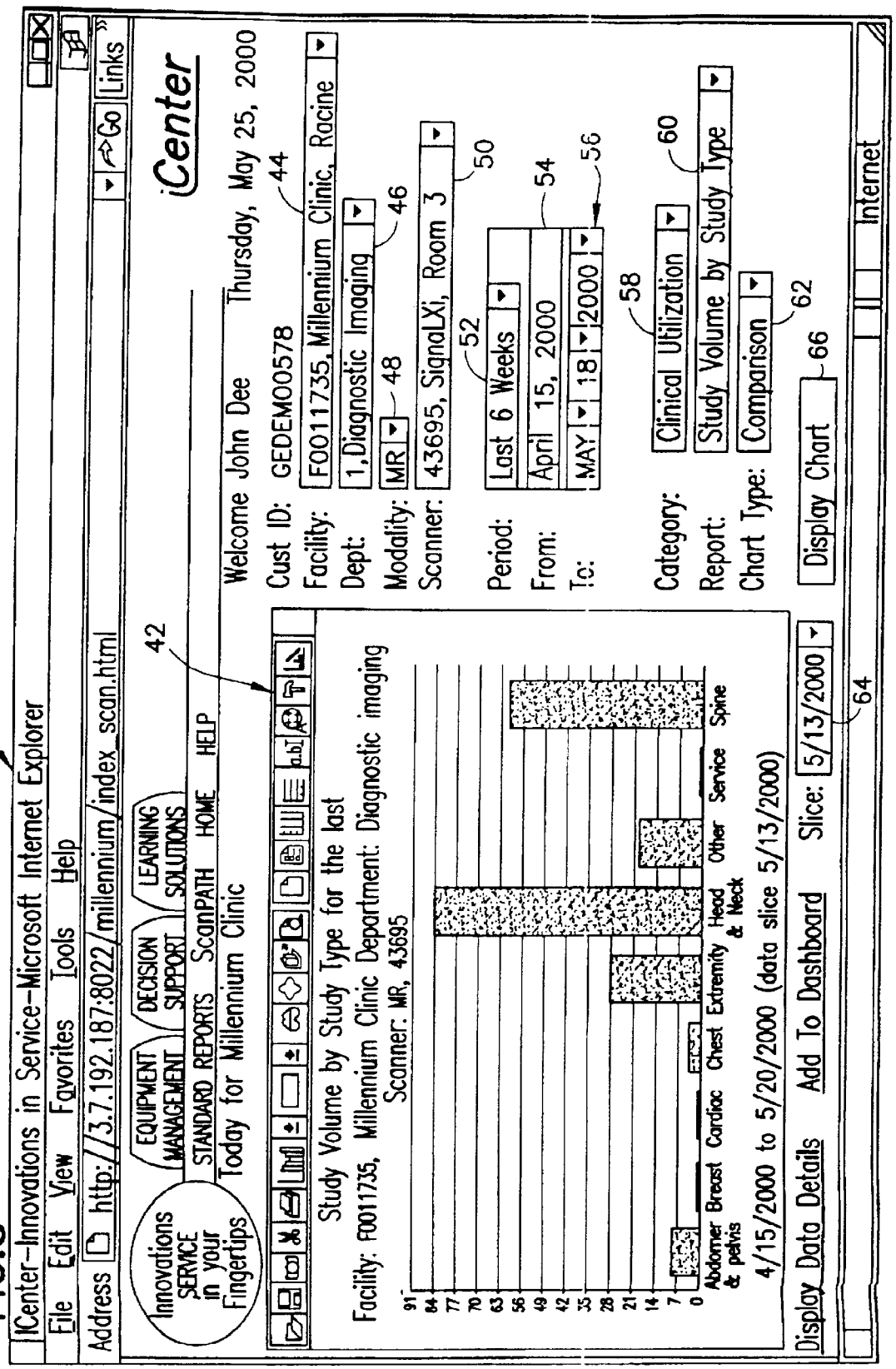
FIG. 3 is a diagram showing a graphical user interface for configuring and then requesting a scanner utilization report from a central service facility via a wide-area network in accordance with the preferred embodiment of the invention.

In accordance with the preferred embodiment of the invention, a customer may access a scanner utilization report for a particular scanner by interacting with a scanner drop-down pick list, which is displayed in response to clicking on display field 50 shown in FIG. 3. A facility is able to obtain reports for utilization of a particular scanner as long as there is a record for that scanner in a database table named FacActiveScanner. The FacActiveScanner table comprises the following columns: Facility ID (FacID), Equipment ID (EquipID) and Contract ID (ContractID). The ability to get a report for a scanner belonging to a facility will depend on the implementation of the scanner drop-down lists in each product module. The scanner drop-down list query in each module will join with the FacActiveScanner table. Only scanners (EquipID=unique ID assigned to a scanner within the Scanner database 30) that exist in the FacActiveScanner table for a given FacID will be displayed in the scanner drop-down lists. The FacID is used to identify a hospital and corporate grouping relationship. In general, only scanners that exist in the FacActiveScanner table will be displayed to users. Preferably a batch process is run nightly to delete records from the FacActiveScanner table when a contract expires.

Each night a batch process is run after midnight to deactivate scanners where there is no longer an active contract covering the generation of scanner utilization reports. The process will query a join of a ContProdFacility database table and a ContFacEquipment database table to find the list of FacID+EquipID that should be deactivated. The query should select records where current date is sooner than ProdEndDate. Records that are in the FacActiveScanner table that are not in the retrieved list should be deleted from the FacActiveScanner table. The ContProdFacility database table comprises the following columns: ContractID, FacID, Product ID (ProductID) (identifying the product or service, e.g., a group of reports, being provided), ProdStartDate (the product start date), ProdEndDate (the product end date), and ProdTermDate (the product termination date). The ContFacEquipment database table comprises the following columns: ContractID, ProductID, FacID and EquipID.

The coding for all of the scanner drop-down lists in all application modules that customers can access will need to have the SQL (Structured Query Language) for the scanner list retrieval join with the FacActiveScanner table and only display scanners that are in the FacActiveScanner table.

Similarly, access to a particular scanner utilization report is controlled using report and chart drop-down pick lists, which are displayed in response to clicking on display fields 60 and 62 respectively (see FIG. 3). Users are able to request reports and charts for only those reports included in the products and modules that they have access to. The ability to get a report will depend on the implementation of the report and chart drop-down lists and/or report links in each product module.

The coding for all report drop-down lists and report links in all application modules that customers can access qualifies the list of reports based on the following: 1) the product that the report belongs to; 2) the module that the report belongs to; and 3) the active products that the selected facility has. To retrieve a list of reports, the SQL will join the ProdReport, FacActiveScanner, ContFacEquipment and ScanPathReports database tables. The ProdReport database table comprises the following columns: ProductID, ModuleID, ReportID, RptCatID (Report Category ID), LastModBy (the user ID of the last service employee to modify this record) and LastModDate (the date on which this record was last modified). The ScanPathReports table comprises the following columns: ReportID, Description, Title, Cube, and MDXQueryName, explained in detail below.

The logic is similar for charts except that the chart drop-down SQL must do an additional table join with the ScanPathCharts database table. The ScanPathCharts table comprises the following columns: ChartID, ReportID, Description, Title, Type, and ChartDefaultSettings, explained in detail below. Only charts that have a Report ID in the list of reports retrieved by the SQL should be displayed in the chart list.

The preferred embodiment of the invention employs a generalized report and chart definition tool based on OLAP (On-Line Application Processing) software. The OLAP-based reporting provides support for a multitude of different reports. The ability to define and create the variety of reports needed by the product requires the development of a generalized mechanism to support the production of reports.

This mechanism needs to be flexible in its configuration in order to make it easy to add additional reports to the product. In addition, these features should be robust enough that they can be used for other application products that utilize OLAP reporting.

The functions described below are features that support the generalization of reports and charts in the OLAP environment. Four types of data are required to support the reports, charts and dashboards that are included in the application. These are: query data, report data, chart data, and dashboard data. The meta data for each of these categories is contained in a separate database table. The term "dashboard" refers to a web page (not shown) which provides users with a quick overview of the most important indicators that the user can monitor, including charts configured by the user using the Standard Reports screen shown in FIG. 3.

The Query Meta Data (MDXQuery) database table contains a list of multidimensional (MDX) queries and the runtime session parameters required to execute them. When a user requests a chart or report, the request will indirectly identify the MDX query to be used to retrieve the data for the selected report. The MDX Query Name is the primary key of a record in the MDXQuery table that contains information about the cube, number of parameters, and the list of parameters that have to be passed to the query. The MDXQuery table comprises the following columns: MDXQueryName, Cube, ParamCount, MDXQuery, Comment, and SessionParameters. This table contains the list of procedures that are used to retrieve data that is used to produce specific reports and charts. The contents of the table include the following: MDXQueryName—the name of an MDX procedure used to retrieve report data; Cube—the name of the OLAP cube that the data will be retrieved from; ParamCount—the number of parameters that have to be passed to this procedure; MDXQuery—the actual SQL code for the data retrieval query, (this query will be different for each report); Comments—any developer comments regarding this procedure; SessionParameters—a comma separated list of parameters (by name) that have to be passed to this procedure in the order that they need to be passed. The data in this table will be maintained using SQL scripts.

The Report Meta Data (ScanPathReports) table contains the list of all OLAP reports that are supported in the application. The contents of the ScanPathReports table include the following: ReportID—a unique ID for each report; Description—a detailed description of the report; Title—the title of the report that is to be displayed on screens; Cube—the name of the OLAP cube that the data will be retrieved from; MDXQueryName—the name of the MDX procedure used to retrieve the data for the report.

The Chart Meta Data (ScanPathCharts) table contains the list of all of the charts that can be produced from a set of report data. The contents of the ScanPathCharts table include the following: ChartID—a unique ID within the Report ID; ReportID—a unique ID for each report; Description—a detailed description of the chart; Title—the title of the chart that is to be displayed on screens; YaxisName—the label for the Y axis to be used in the chart; XaxisName—the label for the X axis to be used in the chart; Type—the style of chart (e.g., trend, bar, pie); ChartDefaultSettings—a string of characters each of which specifies the default setting of a specific chart parameter (e.g., 2D/3D, vertical grid on/off).

In accordance with the preferred embodiment of the invention, a Standard Reports module contains reports and graphs for the first two tiers of scanner utilization report products. The exact set of reports included in Tier 1 and Tier 2 of the product can be defined by Product Management. Preferably, each tier of products will include a respective set of reports provided by this module. All users entitled to access reports are given access to the Standard Reports module.

In accordance with one exemplary preferred embodiment, three categories of Standard Reports are provided in the product. These categories are: Customer Analysis, Clinical Utilization, and Operations Analysis. The desired category can be selected by clicking on a drop-down pick list which is displayed when the user clicks on display field 58 shown in FIG. 3. Each category of report provides the user with a list of reports that contain information related to the category. The product that the customer contracts for will affect the reports in a list. For example, the basic product may only give the user access to a few (e.g., 4) reports while the next level (i.e., tier) of product may give the user access to all of the reports defined in each of the three categories.

The user can login to the security server (14 in FIG. 2) via the Internet. If the user is authorized to access scanner utilization reports, a home web page (not shown in the drawings) will be displayed immediately after login. When the user selects a Standard Reports link on the home web page, the Standard Reports screen 40 (shown in FIG. 3) will be displayed. The parameters on the screen 40 will be set to the last set of parameters that were used by the logged-in user. These parameters will be used to retrieve the appropriate chart, which is displayed in the chart display field 42. The Standard Reports page provides the user with a variety of functions that allow the user to modify the chart displayed. On this page the user has the ability to change every parameter applied to the chart as well as the ability to request all of the available reports and data slices.

The following options are displayed on the Standard Reports screen 40 in the form of drop-down pick lists: the Facility pick list is displayed by clicking on display field 44; the Cost Center or Department pick list is displayed by clicking on display field 46; the Modality pick list (with items MR and CT) is displayed by clicking on display field 48; the Scanner pick list is displayed by clicking on display field 50); the Period pick list (last 5 quarters, last 12 months, last 6 weeks, and last 7 days to be covered by the report or chart) is displayed by clicking on display field 52; the To pick list (the period ending date for the data to be displayed) is displayed by clicking on display field 56); the Report Category pick list (Clinical Utilization, Customer Analysis, Operations Analysis, or performance Analysis) is displayed by clicking on display field 58); the Report pick list is displayed by clicking on display field 60); the Chart Type pick list (Trend or Comparison) is displayed by clicking on display field 62); and the Data Slice pick list (identifying the slice, i.e., subset, of data displayed in the chart) is displayed by clicking on the display field 64. The starting date for the requested time period is automatically determined by the system and is entered in the From field 54.

Each Report Category has its own set of Reports. (Similarly, each Report has its own set of Data Slices.) For example, the drop-down list of reports for the Clinical Utilization category may appear as follows:

Avg Image Count by Radiologist
Avg Image Count by Study Type
Avg Series Count by Study Type
Avg Study Duration by Study Type
Avg Study Image Count by Technologist Contrast Used % by Study Type Study Volume by Hours Study Volume by Operator Study Volume by Physician Study Volume by Radiologist Study Volume by Study Type The drop-down list of reports for the Customer Analysis category may appear as follows:

Exam Volume by Patient Age

Exam Volume by Patient Gender

Exam Volume by Patient Mix

The drop-down list of reports for the Operations Analysis category may appear as follows:

Avg Exam Duration by Patient Mix

Avg Exam Duration by Radiologist

Avg Exam Duration by Technologist

Avg Study Duration by Radiologist

Avg Study Duration by Technologist

Avg Time Between Exams

Avg Time Between Exams by Study Type

Exam Volume by Ordering Physician

Exam Volume by Radiologist

Exam Volume by Technologist

Total Exam Volume

Total Series Volume

Avg Total Duration per Day

Avg Scanner Utilization

After the user has finished selecting all of the desired parameters, the user must click the virtual Display Chart button 66 to activate the system to retrieve the new data and refresh the displayed chart. By clicking on Display Data Details field, the user goes to a Tabular Report page, described below.

In accordance with the preferred embodiment, the following options and functions are implemented on the Standard Reports page.

The list of facilities displayed in the Facility drop-down list should contain the list of facilities meeting the following criteria. The facilities must belong to the selected customer. The facilities must have an active contract for a scanner utilization reporting product. This means the facility must have at least one record in the FacActiveScanner table. The facilities must be able to be accessed by the logged-on user, which criterion is determined via the user's FacGroupID.

The list of cost centers (OrgAreaID) that are displayed in the Department drop-down list should contain the list of cost centers meeting the following criteria. The cost center must have a scanner with an active contract for a scanner utilization reporting product. This is determined using a join between the FacActiveScanner and Equipment tables. The Equipment table comprises the following columns: FacID, EquipID, ModalityCode, EquipActiveInd, ProductLine, SystemID (a unique ID for a scanner for a particular customer at a particular location), SerialNbr, MLN, OrgAreaID, Location, ActivationDate, DeactivationDate, MfgDate, LastUpgradeDate, etc. The cost centers must be able to be accessed by the logged-on user. This is determined from the users OrgAreaGrpID. This is done using a join of the list of OrgAreaID obtained above and the OrgAreaGrpChild table.

The list of modalities should be retrieved from the Modality table. Preferably the list of modalities is qualified according to the modalities of scanners that the OrgArea has. However, the Modality list will display faster if this qualification is omitted.

The list of scanners (EquipID) that are displayed in the Scanner drop-down list should contain the list of scanners meeting the following criteria. The information contained in the Scanner list should be a concatenation of the SystemID and Equipment Name with each element being separated from the previous element by a comma and a space. The scanners must be included in an active contract for a scanner utilization report product. This is determined using a join between the FacActiveScanner and Equipment tables.

The Period selection allows the user to choose a specific number of periods and time dimension. The options that will be provided are: Last 5 Quarters (calendar quarters), Last 12 Months, Last 6 Weeks, and Last 7 Days.

The From field 54 (see FIG. 3) will display the From Date for the selected Period and To Date. The user cannot specify the From Date, the system will determine what it is.

The To field 56 comprises month, day, and year drop-down lists. These fields should be coded to default to the most recent date for which data has been received for the selected scanner. The most recent date that data has been received from a scanner is stored in a ScannerDataFeed table. The most recent date that data was received is stored in a LastExamDate field. The system must retrieve the LastExamDate for the facility and scanner and use it to set the To field when the screen is initialized. Once a user has specified a To date, it should be used until it is changed or the session is ended. Preferably users should not be able to select an invalid date (e.g., Feb 30) from the To drop-down lists. Also users should not be able to select a date beyond the most recent date that data was received for the selected scanner (LastExamDate field).

The Report Category field 58 contains the list of available report categories.

The Report field 60 contains a drop-down list of the reports for the selected Report Category that the user has access to. The Reports drop-down list displayed on the page should be populated with the list of reports that the user is entitled to see based on the active product contracts that the customer has. The list of reports is created by joining several tables, i.e., the ScanPathReports, ProdReport and ContProdFacility tables.

The Chart Type field 62 contains a drop-down list of the different standard types of charts that can be requested, e.g. Trend and Comparison.

The Data Slice field 64 contains a drop-down list of the slices of data that are applicable to the selected data set. In addition, one standard data slice option will be provided for every data set. The standard option is: ALL. The ALL option will display the sum of all the data slices in the chart. For example, if the user has selected the Exam Volume By Patient Type report, the sum of the exam volumes for all patient types will be displayed. The specific slices of data that are contained in the report will also be listed. The slices that are in the report data will depend on all of the parameters that have been specified for the report. The software will interpret the data set to create this list.

The drop-down list selections will apply new parameters that are used to create the MDX query used to retrieve the chart or report data. When the user clicks the Display Chart button 66 the application will perform the following functions: (1) Save the selected items to the ScanOperDB.UserParm table. (2) Use the selected Report and Data Slice parameters to retrieve the MDX Query needed from the ScanPathReports table. (3) Use the MDX Query plus the selected parameters to retrieve the data for the chart from the data cube identified for the MDX Query. The software will use the various dimension tables (e.g., TimeLookup, Facility, Equipment, PatientType) to retrieve the required data based on the parameters the user specified. (4) Refresh the displayed ChartFX object with the data that was retrieved.

The MDX query that should be used to retrieve the data for the report is defined in the ScanPathReports table. When the user selects a report from the Reports drop-down list, the ReportID of the selected report is used to retrieve the MDXQueryName of the required query. The MDXQueryName is then used to retrieve the rest of the information required to satisfy the query from the MDXQuery table. The information retrieved from the MDXQuery table is the following: Cube—the name of the dimensional data cube that contains the data for the report; ParamCount—the number of parameters that the specified MDX query requires; MDXQuery—the full text of the SQL query used for the report; Comment—this is the developer's comment on the query, used for maintenance and code documentation purposes; SessionParameters—this is a comma-delimited string of the parameters that are required by the query in the order that they are to be passed to the query.

When the user selects a report, the chart to be displayed will reflect the user's Chart Type selection in field 62. The ChartID will be determined based on the type of chart selected (e.g., Trend, Comparison) and the ReportID that was selected. The ChartID to be displayed and the parameters that should be used for display are retrieved from the ScanPathCharts table. The data in the record will provide the title of the chart and the default settings for the chart. The user can manipulate the chart using a toolbar in the chart control. The software disables the features that allow the user to modify the data in the chart.

When the user selects the Display Data Details link on screen 40, the detailed data will be displayed in a tabular report on a separate web page (not shown). On this page the user can view the numeric data associated with each data slice in the report for the selected metric in each period. The user can print the report using the browser print functions. The user can also copy the data and paste it into Excel or another desktop application using standard Copy and Paste functions. Preferably the tabular data report displays the full context of the parameters used to generate the report.

When the user selects the Display Data Details link the detailed data will be displayed in a tabular HTML report. The tabular report will include all of the data for every data slice in the report. The data to be displayed in the report is retrieved using the MDX Query for the report as described above.

The present invention is not limited to generating utilization reports based on operational data logging in medical imaging devices. The report generation process disclosed herein can be used to compile and/or summarize operational data from other types of remotely located user-operated electronic devices.

While the invention has been described with reference to preferred embodiments, it will be understood by those skilled in the art that various changes may be made and equivalents may be substituted for elements thereof without departing from the scope of the invention. For example, the Standard Reports screen could also have a virtual Display Report activation button for causing the system to display a tabular report in report display area 42 (shown in FIG. 3) instead of a chart. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

As used in the claims, the term "computer system" is used broadly to include a single computer, server or data processor, or a group of interconnected computers, servers or data processors. As will be readily appreciated by persons skilled in the art, two data processing functions can be implemented as separate software modules or computer programs on separate computers or servers, or as separate software modules or computer programs on the same computer or server.

what is claimed is:

1. A method for downloading a report of scanner utilization from a central service facility to a remote site via a network, comprising the following steps:

transmitting operational data from each scanner in a department via a network to a central service facility for electronic processing, said operational data comprising system data and exam data;

storing said operational data in a multidimensional database at said central service facility;

using a computer at a remote site, a user navigates to a service center home web page that is linked to said central service facility;

displaying a standard reports web page on the display screen of said computer in response to said user selecting a standard reports link on said home web page, said standard reports web page comprising a plurality of user-interactive report content parameter fields that said user can click on to cause a respective drop-down pick list to appear, said fields corresponding to selectable parameters that define the content of a requested report, a first field on said standard reports web page containing an identifier for one of a plurality of stored multidimensional queries, each multidimensional query corresponding to a different report format;

at said central service facility, performing on-line analytical processing on said stored logged data as a function of a multidimensional query and other parameters selected by said user on said standard reports web page; and downloading a report to said computer at said remote site, said report being the result of said on-line application processing step.

2. The method as recited in claim 1, wherein said report is in chart form.

3. The method as recited in claim 2, wherein said standard reports web page comprises an area where said report in chart form is displayed concurrently with said user-interactive fields.

4. The method as recited in claim 1, wherein said report is in tabular form.

5. The method as recited in claim 4, further comprising the step of downloading said report in tabular form as a separate web page to said computer at said remote site.

6. The method as recited in claim 1, wherein a second field on said standard reports web page containing an identifier for one of a plurality of scanners, further comprising the step of verifying at said central service facility that said selected scanner identifier is included in a database of scanner identifiers identifying authorized scanners.

7. The method as recited in claim 1, wherein said operational data in said multidimensional database is XML-encoded.

8. A networked system comprising:

data collection server means for collecting data;

a multiplicity of scanners each programmed to log specified operation-related data and send that logged data to said data collection server means;

a multidimensional database for storing logged data collected by said data collection server;

a remote customer access station comprising a browser; and report generation web server means for downloading a report of scanner utilization to said remote customer access station, said report generation server means being programmed to download a standard reports web page for display at said customer access station in response to a customer selecting a standard reports link on a home web page, said standard reports web page comprising a plurality of user-interactive report content parameter fields that said customer can click on to cause a respective drop-down pick list to appear, said fields corresponding to selectable parameters that define the content of a requested report, a first field on said standard reports web page containing an identifier for one of a plurality of stored multidimensional queries, each multidimensional query corresponding to a different report format, and being further programmed to perform on-line analytical processing on said stored logged data as a function of a multidimensional query and other parameters selected by said user on said standard reports web page and then download said report to said customer access station, said report being the result of said on-line application processing.

9. The system as recited in claim 8, wherein said report is in chart form.

10. The system as recited in claim 9, wherein said standard reports web page comprises an area where said report in chart form is displayed concurrently with said user-interactive fields at said customer access station.

11. The system as recited in claim 8, wherein said report is in tabular form.

12. The system as recited in claim 11, wherein said report generation web server means is programmed to download said report in tabular form as a separate web page to said customer access station.

13. The system as recited in claim 12, wherein a second field on said standard reports web page contains an identifier for one of a plurality of scanners, wherein said report generation web server means is further programmed to verify that said selected scanner identifier is included in a database of scanner identifiers identifying authorized scanners.

14. The system as recited in claim 8, wherein said logged data in said multidimensional database is XML-encoded.

15. A system comprising a central computer system programmed to generate reports in response to report requests, a remote customer access station programmed to transmit report requests following inputs by a user, and a communications link between said computer system and said customer access station via which said report requests are transmitted to said central computer system and via which said generated reports are transmitted to said customer access station, wherein said programming in said central computer system and in said remote customer access station enables the following algorithm:

a standard reports web page is displayed at said remote customer access station, said standard reports web page comprising a plurality of user-interactive report content parameter fields that said user can click on to cause a respective drop-down pick list to appear, said fields corresponding to selectable parameters that define the content of a requested report, a first field on said standard reports web page containing an identifier for one of a plurality of stored multidimensional queries, each multidimensional query corresponding to a different report format;

said central computer system performs on-line analytical processing on scanner utilization data stored in a multidimensional database as a function of a multidimensional query and other parameters selected by said user on said standard reports web page; and said central computer system downloads a report to said remote customer access station, said report being the result of said on-line application processing of said scanner utilization data.

16. The system as recited in claim 15, wherein said central computer system is further programmed to validate said user and determine said user's access privileges before processing a report request.

17. The system as recited in claim 16, wherein said central computer system comprises a report server programmed to process report requests and a security server programmed to block access to said report server if the user is not validated.

18. The system as recited in claim 15, wherein said report is in chart form.

19. The system as recited in claim 18, wherein said standard reports web page comprises an area where said report in chart form is displayed concurrently with said user-interactive fields at said customer access station.

20. The system as recited in claim 15, wherein said report is in tabular form.

21. The system as recited in claim 20, wherein said central computer system is programmed to download said report in tabular form as a separate web page to said customer access station.

22. The system as recited in claim 15, wherein a second field on said standard reports web page contains an identifier for one of a plurality of scanners, wherein said central computer system is further programmed to verify that said selected scanner identifier is included in a database of scanner identifiers identifying authorized scanners.

23. The system as recited in claim 15, wherein said scanner utilization data in said multidimensional database is XML-encoded.

24. The system as recited in claim 15, further comprising a multiplicity of scanners at remote locations, each scanner being programmed to upload its scanner utilization data to said central computer system, said central computer system being further programmed to continually store uploaded scanner utilization data in said multidimensional database.

* * * * *